United States Patent [19]

Singh

[11] 4,150,030

[45] Apr. 17, 1979

[54] 3-ACYL-4-ETHYL-2-OXAZOLONES AND OXAZOLIDINONES

[75] Inventor: Balwant Singh, Stamford, Conn.

[73] Assignee: American Cyanamid Company, Stamford, Conn.

[21] Appl. No.: 786,906

[22] Filed: Apr. 12, 1977

Related U.S. Application Data

[63] Continuation-in-part of Ser. No. 642,944, Dec. 22, 1975, abandoned.

[51] Int. Cl.$^2$ .................. C07D 263/26; C07D 263/38
[52] U.S. Cl. ........................... 260/307 C; 260/307 A; 260/558 R; 260/561 R; 260/584 R; 560/106; 560/113; 560/250; 560/253
[58] Field of Search .................... 260/307 C, 642, 944

[56] References Cited
PUBLICATIONS

Palomo Coll — C.A. 81, 152210d (1974) — Abstract of German Offen. 2,408,171.
Elderfield — "Heterocyclic Compounds" — vol. 5 — Wiley & Sons, Inc. — (1975) — pp. 400–401.

*Primary Examiner*—Raymond V. Rush
*Attorney, Agent, or Firm*—Claude J. Caroli

[57] ABSTRACT

This invention relates to the preparation of optically active d-2-aminobutanol by catalytic asymmetric reduction of appropriate dehydro precursors to produce selectively the desired isomer. The same substrates can also be used to prepare the dl-mixture using optically inactive catalysts. The novel substituted-4-ethyl-4-oxazolin-2-one and substituted-4-ethyl-2-oxazolidinone compounds of this invention are useful as intermediates in the production of the antituberculosis drug ethambutol (Myambutol ®).

16 Claims, No Drawings

3-ACYL-4-ETHYL-2-OXAZOLONES AND OXAZOLIDINONES

This application is a continuation-in-part of my co-pending application Ser. No. 642,944, filed Dec. 22, 1975, and now abandoned.

BACKGROUND OF THE INVENTION

The compound of d-2-aminobutanol is currently prepared by resolution of its racemic mixture with L(+)-tartaric acid. Approximately fifty percent (50%) of the material is washed in the l-stream together with the resolving agent because it is unavailable for recycle. A method aimed at direct synthesis of the desired d-isomer would constitute a great advance in the art.

Synthesis of optically active amino acids (II) by asymmetric hydrogenation of their dehydro precursors is well known in the art; W. S. Knowles, M. J. Sabacky and B. D. Vineyard, Chem. Commun., 1445 (1963), 10 (1972); W. S. Knowles, M. J. Sabacky and B. D. Vineyard, Ann. N.Y. Acad. Sci., 172, 232 (1970); Chem. Engineering News, Feb. 7, 1972, p. 4; Chem. Week, Feb. 9, 1972, p. 41; T. P. Dang and H. B. Kagan, Chem. Commun. 481, (1971); H. B. Kagan and T. P. Dang, J. Am. Chem. Soc., 91, 6429 (1972).

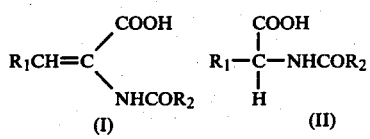

Asymmetric hydrogenation of α-acylaminocrotonic acid

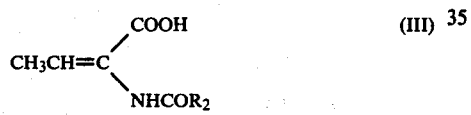

followed by reduction of the carboxyl group to hydroxymethyl could in principle result in d-2-aminobutanol, but the reduction conditions for the second step are rather severe. Alternate routes involving asymmetric hydrogenation of α-acylamino crotyl alcohol and its O-acyl derivatives (IV) were investigated.

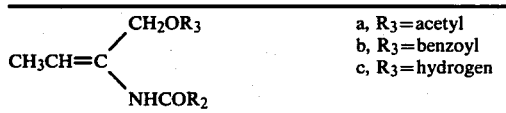

a, $R_3$=acetyl
b, $R_3$=benzoyl
c, $R_3$=hydrogen

The O-acetate (IVa) and the O-benzoate (IVb) however, suffered hydrogenolysis of the ester groups and the products formed were acylamino alkanes rather than the alcohol esters. Hydrogenolysis can be prevented by hydrogenating the free alcohol (IVc) prepared from either (IVa) or (IVb) by treatment with ammonia or amines.

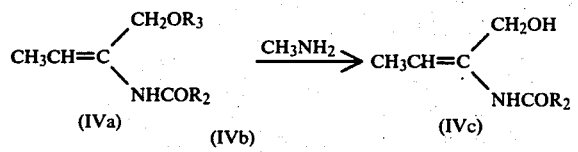

Enamido alcohols such as VII are difficult to prepare. Reported reactions involves lithium borohydride or calcium borohydride reduction of azlactones such as (VI):

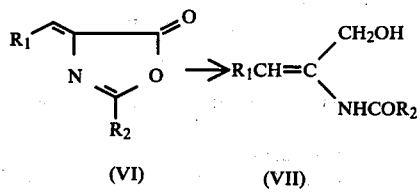

This reaction works well only with azlactones where $R_1$ is phenyl or another bulky substituent, and is characterized by generally poor yields.

The synthesis of the instant invention, as set forth below, has certain novel elements.

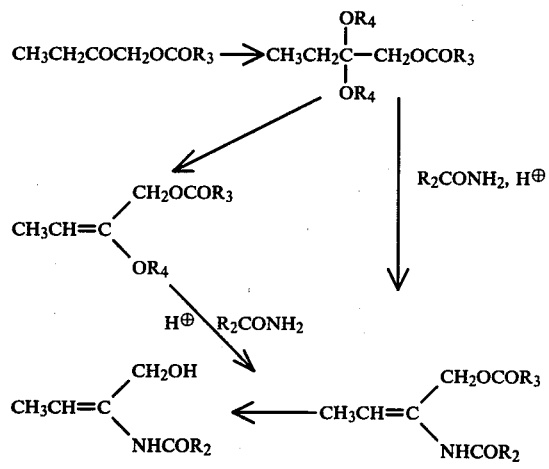

$R_4$ = loweralkyl
$R_3$ = loweralkyl, aryl and the like
$R_2$ = loweralkyl or aryl The second route is based on asymmetric reduction of 4-ethyl-oxazolinones. Asymmetric or nonasymmetric hydrogenation of 4-ethyl oxazolinones (VII) to 4-ethyl oxazolidones (VIII) which can be hydrolyzed respectively to d-2-aminobutanol or dl-2-aminobutanol has not been reported in the literature. The synthetic route is novel while the catalysts are conventional or newly discovered by other workers. The novel synthetic routes of the instant invention provide flexibility for the production of d-2-aminobutanol as well as dl-2-aminobutanol in that they may both be prepared from the same substrate using chiral or achiral catalysts.

The most closely related art of which Applicant is aware is the Abstract of German Offen. No. 2,408,171, which discloses certain compounds of the formula:

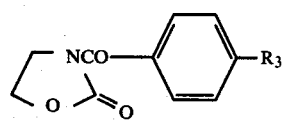

SUMMARY OF THE INVENTION

This invention relates to the direct synthesis of d-2-aminobutanol via unsaturated precursors by hydrogenation in the presence of optically active catalysts derived from rhodium chloride and optically active phosphines. The novel synthesis avoids the use of resolving agents and also avoids the wasteful recycling of the undesired isomer thereby significantly reducing the production costs of d-2-aminobutanol, the key intermediate for the production of ethambutol (Myambutol ®).

DISCLOSURE

The reduction of eneamido moieties using chiral phosphine-rhodium (I) complexes has been shown to proceed in high optical selectivities; W. S. Knowles et al., supra; H. B. Kagan et al., supra. The asymmetric hydrogenation of 4-ethyl-2-oxazolinone (VIIa), which contains an eneamido moiety, using (+)-DIOP-RhCl catalyst, results in the formation of 4-ethyl-2-oxazolidone (VIIIa) which is hydrolyzable to d-2-aminobutanol as shown below:

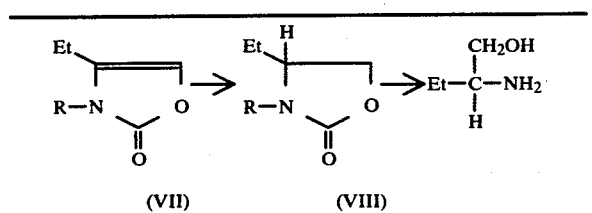

a, R = hydrogen
b, R = acetyl
c, R = benzoyl
d, R = o-chlorobenzoyl
e, R = o-anisoyl
f, R = p-anisoyl
g, R = o-toluoyl
h, R = o-carboxybenzoyl
i, R = o-hydroxybenzoyl The literature reveals that while (VIIa) is unknown, oxazolinones with substituents other than 4-ethyl have been reported to be formed in 60–80% yield by the reaction of 2-ketoalcohols and urethane in refluxing dimethylformamide as well as by reaction with carbamoyl chloride; R. Gompper, Chem. Ber. 89, 1748 (1956). The compound (VIIa) may be produced by the above method with about 0–60% yield, but the procedure is quite tedious and the crude oxazolinone is difficult to purify. A simpler procedure for making the (VIIa) compound consists of reacting 2-ketobutanol with cyanic acid (prepared in situ from potassium cyanate and acetic acid) at 0° to 25° C. to form the desired oxazolinone in about 70% yield.

The reduction of the (VIIa) oxazolinone using (+)DIOP-rhodium chloride as a catalyst proceeds smoothly but with a low optical yield. Optical yield is defined as the percent of excess of one enantiomer over the other. Catalytic asymmetric hydrogenation of compound (VIIb) under conditions somewhat similar to those used for compound (VIIa) (40° C., 50 psig hydrogen) using (+)-DIOP-rhodium chloride catalyst (substrate:catalyst ratio=100:1) proceeds with an optical yield of 17.5% to afford 3-acetyl-4-ethyl-oxazolinone (VIIIb). The compound (VIIc) is obtained from the benzoylation of (VIIa) with benzoyl chloride and pyridine in benzene. When benzoylation is carried out at room temperature (using triethylamine or pyridine as base catalysts) the initial product of the reaction is 2-benzoyloxy-4-ethyloxazole, a product isomeric with VIIc. By raising the temperature (steambath) or by isolating the material and heating it to reflux in hexane or other inert solvents, the desired 3-benzoyl-4-ethyloxazolinone VIIc is obtained. Hydrogenation of 2-benzoyloxy-4-ethyloxazole at higher than room temperatures may also result in VIIIc because under these conditions the isomeric oxazole derivative will isomerize to oxazolinone VIIc which will follow the normal course of reduction to give VIIIc. Using (+)-DIOP-rhodium chloride as a catalyst, the compound (VIIc) is quantitatively reduced (60° C., 60 psig hydrogen, substrate:catalyst=60:1) to yield the crude compound (VIIIc).

The coordinative interactions of the substrate with the catalyst together with steric and dipolar forces are undoubtedly of critical importance and to some degree they are controlled by such parameters as temperature, hydrogen pressure, solvent polarity, etc. The literature indicates that lower hydrogen pressures and temperatures in general favor higher optical yields.

To assess the relative importance of reaction parameters on the asymmetric reduction of oxazolinone ring systems, several asymmetric reductions of compound (VIIc) were carried out under several different conditions. The results of these asymmetric reductions are summarized in Table I.

TABLE I

| | Reduction of Oxazolinones Using Rh(COD*)Cl-(+)-DIOP** Catalyst | | | | |
|---|---|---|---|---|---|
| Oxazolinone I | Solvent | H₂ (Psig) | Temp. ° C. | Subst/Rh | Optical Yield |
| VIIa | C₆H₆—EtOH (1:1) | 70 | 50 | 100 | 5 |
| VIIb | C₆H₆—EtOH (1:1) | 60 | 25 | 66 | 15.2 |
| VIIc | C₆H₆—EtOH (1:1) | 60 | 50 | 65 | 33.5 |
| VIIc | C₆H₆—EtOH (1:1) | 50 | 40 | 62 | No Reaction (40 hrs) |
| VIIc | C₆H₆—EtOH (1:4) | 60 | 50 | 80 | 19.5 |
| VIIc | EtOH | 60 | 50 | 80 | 26.1 |
| VIIc | C₆H₆ | 6 | 25 | 143 | No Reaction (90 hrs) |
| VIIc | C₆H₆ | 7 | 50 | 144 | 25.6 |
| | Using [Rh(COD)*DIOP]⊕ BF₄⊖ Catalyst | | | | |
| VIIc | C₆H₆ | 60 | 25 | 88 | 7.5 |

*COD = 1,5-cyclooctadiene
**Actual catalytic species = (+)-DIOP-RhCl

The results indicate that although gross variation in optical yield occur, they appear to be more sensitive to the structure of the substrate than to changes in solvent, hydrogen pressure or temperature.

The reduction of compound (VIIc) using more hindered catalysts derived from xylyl-DIOP (m-xylyl analog of DIOP) in the systems studied so far gives slightly lower optical yields than those obtained with DIOP-rhodium chloride catalysts.

To determine the importance of stereoelectronic factors on the course of asymmetric reductions several 3-acyloxazolinones were reduced to the corresponding oxazolidones. The results of these experiments are summarized in Table II.

TABLE II

Asymmetric Hydrogenation of Oxazolinones

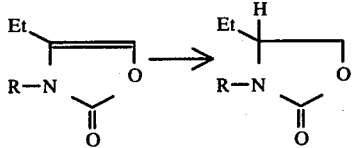

| R | Solvent | Catalyst | Temp. 0° C. | H₂ Press. (psig) | Time (Hrs) | Opt. Yield % |
|---|---|---|---|---|---|---|
| hydrogen | Benzene:Ethanol (1:1) | (+)-DIOP-RhCl | 50 | 60 | 12 | 5 |
| acetyl | Benzene | (+)-DIOP-RhCl | 40 | 50 | 12 | 17.5 |
| benzoyl | Benzene | (+)-DIOP-RhCl | 25 | 10 | 18 | 39 |
| benzoyl | Benzene | (+)-DIOP-RhCl | 50 | 10 | 18 | 23 |
| benzoyl | Benzene | (+)-DIOP-RhCl | 25 | 2 | 50 | 19 |
| o-chlorobenzoyl | Benzene | (+)-DIOP-RhCl | 25 | 10 | 50 | No Reaction |
| o-chlorobenzoyl | Benzene | (+)-DIOP-RhCl | 50 | 60 | 50 | No Reaction |
| p-anisoyl | Benzene | (+)-DIOP-RhCl | 50 | 60 | 50 | 17 |

SPECIFIC DISCLOSURE

The following examples illustrate in detail the specific compounds of the present invention and the preparation of their intermediates as well as the novel method of catalytic asymmetric reduction.

EXAMPLE 1

Preparation of DIOP-RhCl Catalyst

The catalyst solution is prepared from 21.1 mg. of chloro Rh(I) cyclooctadiene dimer (ROC-RIC Corp.), 60 mg. of (+)-DIOP and 5 ml. of benzene following Kagan's directions, by stirring for 15 minutes under argon. [H. B. Kagan and T. P. Dang, J. Am. Chem. Soc. 91, 6429 (1972)].

EXAMPLE 2

Asymmetric Hydrogenation of 4-ethyl-oxazoline-2-one

A sample of the oxazolinone (339 mg.) is dissolved in 10 ml. of ethanol-benzene (2:1). The catalyst solution (prepared from 10.56 mg. of [RhCl(COD)₂]₂ and 35 mg. of (+)-DIOP) is added and the mixture hydrogenated at 50° C. and 60 psig of hydrogen overnight. Nuclear Magnetic Resonance analysis indicates that hydrogenation occurs quantitatively. A 2% solution of the resulting oxazolidone in absolute ethanol shows a rotation of 0.03° corresponding to an optical yield of about 5%.

The hydrogenation material is hydrolyzed with aqueoud ethanolic sodium hydroxide (2 g. sodiumhydroxide in 5 ml. of water and 5 ml. ethanol) to give 2-aminobutanol. The material is isolated from the aqueous solution by extraction with ether. A 2% solution of the crude 2-aminobutanol sample shows a rotation of 0.08° corresponding to an optical yield of about 5%.

EXAMPLE 3

Preparation of 4-ethyl-4-oxazolin-2-one

Potassium cyanate (60 g.) is added to a stirred and cooled (3° C.) solution of 1-hydroxy-2-butanone (30 g.) (2-ketobutanol) in 500 ml. of anhydrous ether. Acetic acid (30 ml.) is added over a period of 10 minutes and the mixture stirred for an additional 3.5 hours whereupon the temperature rises to 16° C. The mixture is kept at room temperature overnight. The ether solution is removed from the solid by decantation. The solid residue is washed twice with ether and discarded. The combined ether solutions is evaporated to leave a yellow oily residue (6.7 g.). The Infrared and Nuclear Magnetic Resonance are compatible with the desired material and the latter indicated its purity to be about 82%.

EXAMPLE 4

Preparation of 2-Acetyl-4-ethyloxazoline-2-one

Crude 4-ethyloxazolin-2-one is refluxed with acetic anhydride for three hours, poured into water, extracted into ether and distilled. The product (56% pure by both GLC and Nuclear Magnetic Resonance) is reduced with (+)-DIOP-RhCl catalyst (prepared in situ as in Example 2) to give impure 2-acetyl-4-ethyloxazolidine-2-one. Comparison of the optical rotation of this product with that of authentic d-2-acetyl-4-ethyloxazolidine-2-one shows and optical yield of 17.5%. Hydrolysis gives d-2-aminobutanol with an optical purity of 12.7%. These values are consistent with about a 15% optical yield in the hydrogenation.

EXAMPLE 5

Preparation of 2-Benzoyl-4-ethyloxazoline-2-one

Crude 4-ethyloxazoline-2-one (22.6 g., 0.2 mole) in 100 ml. of benzene is cooled in ice while benzoyl chloride is (30.0 g., 0.212 mole) added rapidly. Triethylamine (23 g. 0.227 mole) in 100 ml. of benzene is added slowly. Triethylamine hydrochloride is filtered off after warming to room temperature. This gives 2-benzoyloxy-4-ethyloxazole, a product isomeric with the desired product. On refluxing for 24 hours in cyclohexane the 2-benzoyl-4-ethyloxazole isomerizes to the desired product which is recrystallized from hexane to give 14 g. (0.0645 mole) 32%.

EXAMPLE 6

Preparation of 4-Ethyl-3-p-methoxybenzoyl-4-oxazolin-2-one

The material is prepared by the reaction of 4-ethyl-4-oxazolin-2-one with p-methoxybenzoyl chloride in pyridine. Pyridine hydrochloride is removed by filtration, solvents removed under reduced pressure and the residue distilled under vacuum. The distilled material (130°–180°/0.2 mm) is obtained as a yellow oil which solidifies. The solid is twice recrystallized from ethanol and the crystalline product washed with petroleum ether to give almost colorless crystals (m.p. 101°–103° C.) of the desired material.

EXAMPLE 7

Preparation of 4-Ethyl-3-o-chlorobenzoyl-4-oxazolin-2-one

A solution of o-chlorobenzoyl chloride (1.93 g.) and 4-ethyl-4-oxazolin-2-one (1.13 g.) in 30 ml. of benzene is cooled to 10° C. and reacted with 1.21 g. of triethylamine dissolved in 5 ml. of benzene. The reaction mixture is stirred at room temperature for 1 hour. The excess triethylamine and benzene is removed under reduced pressure to leave a light yellow oil (2.4 g.) which is triturated with ethanol whereupon a crystalline solid separates. The solid is removed and washed with a small amount of cold ethanol and dried. Yield 0.3 g.; m.p. 110°–112° C.

EXAMPLE 8

Asymmetric hydrogenation of 4-ethyl-3-p-methoxybenzoyl-4-oxazolin-2-one

Reduction of the title compound with a chiral rhodium complex leads to a material with Infrared and Nuclear Magnetic Resonance spectra essentially identical to that of known 3-benzoyl-4-ethyloxazolidine-2-one. The specific rotation of +48.2° corresponds to 32.8% optical yield. (100% Pure $[\alpha]_D^{25} = +147°$, c=1%, ethanol). Base hydrolysis, followed by acidification, gives d-2-aminobutanol hydrochloride ($[\alpha]_D^{25} = +3.81°$). The specific rotation corresponds to 34% optical yield ($[\alpha]_D^{25}$ for the pure compound $= +11.2°$, c=10%, water).

EXAMPLE 9

Preparation of methylcyclohexylorthomethoxyphenylphosphine Catalyst

The catalyst solution is prepared by dissolving $RhL_3Cl_3$ (L=tertiary phosphine) in a benzene-ethanol (1:1 v/v) solvent system containing triethylamine (3.5 moles per mole of rhodium complex) and pressurizing with hydrogen gas. The hydrogenation is carried out in a bomb equipped with a pressure gauge and thermocouple at an initial pressure of 300–400 lb in$^{-2}$ and temperatures ranging from 25°–80° C.; W. S. Knowles, M. J. Sabocky, and B. D. Vineyard, Homogeneous Catalysis II, Adv. Chem. Ser. (ACS), No. 132, 274 (1974).

I claim:

1. A compound of the formula:

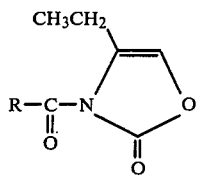

wherein R is selected from the group consisting of $C_1$–$C_6$ alkyl, phenyl, tolyl, anisyl, carboxyphenyl and hydroxyphenyl.

2. A compound according to claim 1, wherein R is selected from the group consisting of p-anisyl, carboxyphenyl and hydroxyphenyl.

3. A compound according to claim 1, wherein R is selected from the group consisting of $C_1$–$C_6$ alkyl, phenyl, and tolyl.

4. A compound according to claim 3, wherein R is selected from the group consisting of methyl, phenyl, and tolyl.

5. The compound according to claim 2, 3-p-anisoyl-4-ethyl-4-oxazolin-2-one.

6. The compound according to claim 4, 3-acetyl-4-ethyl-4-oxazolin-2-one.

7. The compound according to claim 4, 3-benzoyl-4-ethyl-4-oxazolin-2-one.

8. The compound according to claim 4, 3-o-toluoyl-4-ethyl-4-oxazolin-2-one.

9. A compound of the formula:

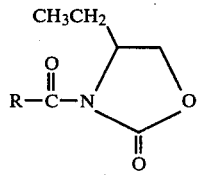

wherein R is selected from the group consisting of $C_1$–$C_6$ alkyl, phenyl, tolyl, anisyl, carboxyphenyl and hydroxyphenyl.

10. A compound according to claim 9, wherein R is selected from the group consisting of anisyl, carboxyphenyl and hydroxyphenyl.

11. A compound according to claim 9, wherein R is selected from the group consisting of $C_1$–$C_6$ alkyl, phenyl, and tolyl.

12. A compound according to claim 11, wherein R is selected from the group consisting of methyl, phenyl, and tolyl.

13. The compound according to claim 9, 3-p-anisoyl-4-ethyl-2-oxazolidinone.

14. The compound according to claim 12, 3-acetyl-4-ethyl-2-oxazolidinone.

15. The compound according to claim 12, 3-benzoyl-4-ethyl-2-oxazolidinone.

16. The compound according to claim 12, 3-o-toluoyl-4-ethyl-2-oxazolidinone.

* * * * *